(12) United States Patent
Schneider

(10) Patent No.: US 8,747,393 B2
(45) Date of Patent: *Jun. 10, 2014

(54) MEDICAL INSTRUMENT

(75) Inventor: Sven Schneider, Tuttlingen (DE)

(73) Assignee: Karl Storz GmbH & Co. KG (DE)

(*) Notice: Subject to any disclaimer, the term of this patent is extended or adjusted under 35 U.S.C. 154(b) by 227 days.

This patent is subject to a terminal disclaimer.

(21) Appl. No.: 12/817,687

(22) Filed: Jun. 17, 2010

(65) Prior Publication Data

US 2010/0324593 A1    Dec. 23, 2010

(30) Foreign Application Priority Data

Jun. 17, 2009   (DE) .......................... 10 2009 025 663

(51) Int. Cl.
  *A61B 17/00*   (2006.01)
  *B62K 21/26*   (2006.01)

(52) U.S. Cl.
  USPC ............................... 606/1; 606/205; 74/551.9

(58) Field of Classification Search
  USPC .................... 606/1, 120, 148, 203, 210–112,
    606/205–211, 167; 81/177.2, 300, 342,
    81/370, 385, 405, 408, 427.5; 30/194,
    30/232, 233, 254, 260, 298, 340; 74/551.9
  See application file for complete search history.

(56) References Cited

U.S. PATENT DOCUMENTS

| | | | |
|---|---|---|---|
| 5,060,381 A * | 10/1991 | Taberlet | 30/232 |
| 5,143,455 A * | 9/1992 | Squyres | 384/97 |
| 5,143,456 A * | 9/1992 | Jordens et al. | 384/275 |
| 5,234,460 A | 8/1993 | Stouder, Jr. | |
| 5,375,331 A * | 12/1994 | Meixner | 30/275.4 |
| 5,430,941 A * | 7/1995 | Lin | 30/260 |
| 5,591,176 A * | 1/1997 | Henderson et al. | 606/137 |
| 5,659,959 A * | 8/1997 | Parlowski | 30/232 |
| 5,928,263 A * | 7/1999 | Hoogeboom | 606/205 |
| 6,212,780 B1 * | 4/2001 | Huang | 30/232 |
| 6,260,277 B1 * | 7/2001 | Wu | 30/232 |
| 6,367,155 B2 * | 4/2002 | Homann | 30/140 |
| 6,393,703 B1 * | 5/2002 | Wu | 30/232 |
| 2005/0119692 A1 * | 6/2005 | Szabo | 606/205 |
| 2007/0016248 A1 * | 1/2007 | Cuschieri et al. | 606/205 |
| 2009/0082795 A1 * | 3/2009 | Blocher et al. | 606/167 |

FOREIGN PATENT DOCUMENTS

| | | |
|---|---|---|
| DE | 4428479 A1 | 2/1996 |
| DE | 10222042 B3 | 1/2004 |
| DE | 102005027418 A1 | 12/2006 |
| DE | 202005020819 U1 | 8/2008 |

OTHER PUBLICATIONS

European Search Report; Application No. EP 10 00 6012; Aug. 24, 2010; 4 pages.

* cited by examiner

*Primary Examiner* — Darwin Erezo
*Assistant Examiner* — Richard Louis
(74) *Attorney, Agent, or Firm* — St. Onge Steward Johnston & Reens LLC

(57) ABSTRACT

A medical instrument with a shaft on whose distal end a tool is positioned and on whose proximal end a handle is positioned consisting of at least two gripping members, such that the tool can be actuated by a gripping member of the handle that is moveably configured and such that at least one gripping member of the handle consists of a rigid partial area and a pivotable partial area that can pivot around the rigid partial area. To create a medical instrument that is of simple structure and can be quickly and thoroughly cleaned, it is proposed with the invention that the pivotable partial area of the gripping member can be removably affixed to the rigid partial area of the gripping member by a catch mechanism.

13 Claims, 3 Drawing Sheets

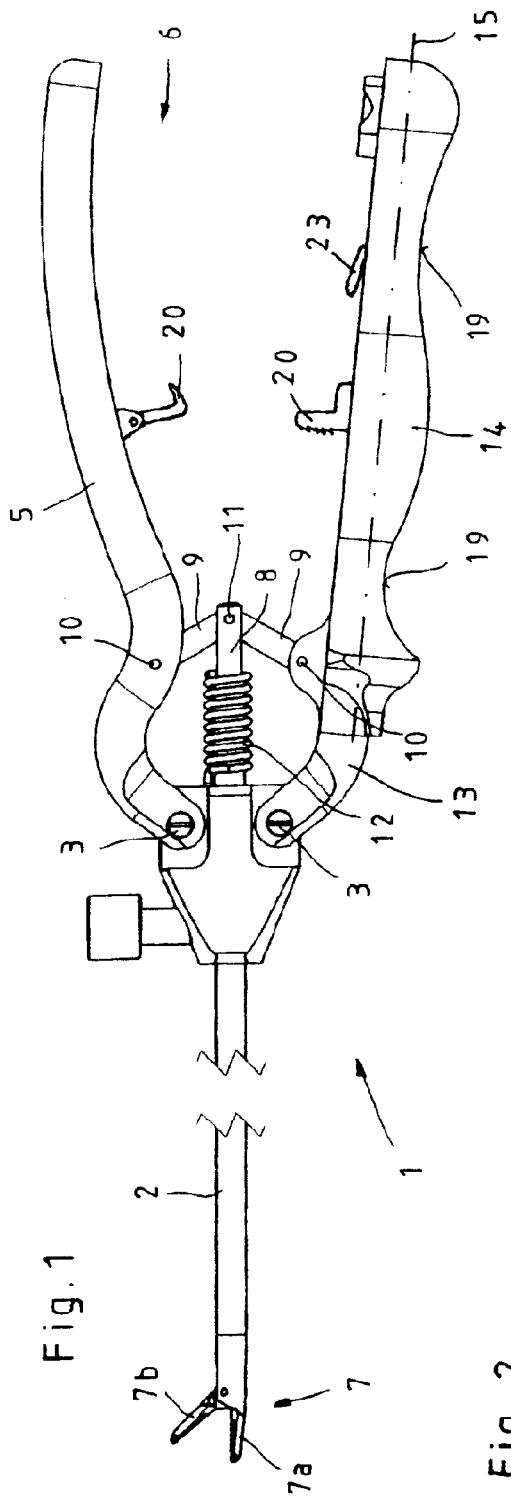
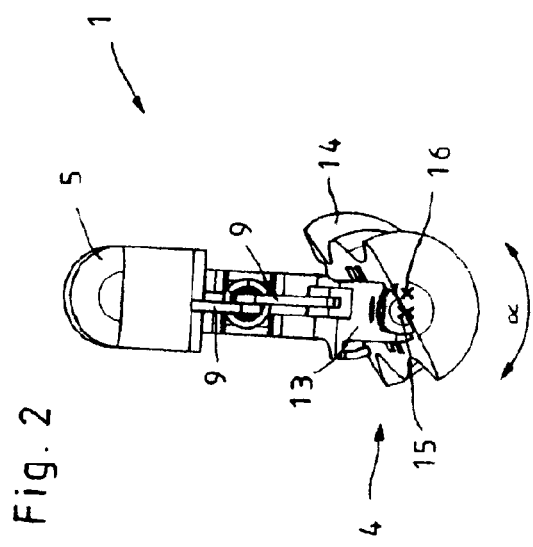

MEDICAL INSTRUMENT

CROSS-REFERENCE TO RELATED APPLICATIONS

The present application claims priority of German patent application No. 10 2009 025 663.6 filed on Jun. 17, 2009, the content of which is incorporated herein by reference.

FIELD OF THE INVENTION

The invention relates to a medical instrument with a shaft on whose distal end a tool is positioned and on whose proximal end a handle is positioned consisting of at least two gripping members, such that the tool can be actuated by a moveably configured gripping member of the handle and such that at least one gripping member of the handle consists of a rigid partial area and a partial area that can pivot around the rigid partial area.

BACKGROUND OF THE INVENTION

A generic medical instrument is known, for instance, from DE 10 2005 027 418 A1. Owing to the configuration of one partial area of a handle as a partial area that can pivot around the longitudinal axis of the gripping member, it is possible with this known instrument, without releasing the handle or reaching around it, first of all to vary the position of the handle in the hand in such a way that no pressure spots result on the operator's hand and, secondly, to ensure a constantly optimal position of the gripping members to the operator's hand and finger position, in order to allow the best possible application of force by the hand to the instrument.

This type of pivotable configuration of a gripping member of the handle has proved itself in the art; however, it involves very considerable installation and dismantling effort to remove the pivotable partial area of the gripping member from the rigid gripping member for cleaning purposes and/or to reconnect it again.

Consequently it is the object of the invention to produce a medical instrument that is simple in structure and can also be cleaned quickly and thoroughly.

SUMMARY OF THE INVENTION

The accomplishment of this object by means of the invention is characterized in that the pivotable partial area of the gripping member can be removably secured by a catch mechanism to the rigid partial area of the gripping member and that the catch mechanism comprises a catch hook, which is configured so that it can be actuated by a push-button.

Owing to the inventive configuration of a catch mechanism for installing and dismantling the pivotable partial area, it is possible without use of tools to remove the pivotable partial area easily and rapidly, in particular for cleaning purposes, and to secure it again to the rigid partial area.

According to a practical embodiment of the invention, it is proposed that the catch mechanism should comprise a spring-loaded push-button that is equipped with a catch hook and is positioned on one of the components that are to be connected by catching with one another, and a locking element, in particular a lock bolt, that is positioned on the other component and corresponds with the catch hook. This configuration of the catch mechanism as a catch hook and corresponding locking element, in particular a lock bolt, constitutes an embodiment of the inventive catch mechanism that is particularly simple to produce and to handle.

With a preferred embodiment of the invention, it is proposed that the catch mechanism should include a sliding and locking bushing that can be secured onto the pivotable partial area and that serves as a proximal pivot bearing for the pivotable partial area. Owing to the use of the sliding and locking bushing, the catching functions of the rigid partial area and pivotable partial area components, as well as the pivotable mounting of the pivotable partial area, are combined in a single module. According to a practical embodiment it is proposed that the push-button should be mounted on the sliding and locking bushing.

In order, first, to make possible a smooth-running pivoting motion of the pivotable partial area around the rigid partial area and, second, to be able to adjust the friction resistance individually, it is further proposed with the invention that the sliding and locking bushing should include a pivot bearing that is non-pivotably connected with the push-button as well as a sliding bushing that interacts with the pivot bearing and is connected non-pivotably with the pivotable partial area.

To achieve the least possible abrasive pivot mounting, it is proposed with the invention that at least the contact surfaces of the pivot bearing and of the sliding bushing should be made of a slippery material. Alternatively to making only the contact surfaces from a slippery material, it is also possible of course to produce the pivot bearing and the sliding bushing completely of a slippery material, such as for example Teflon®, or else to coat the contact surfaces with the slippery material.

The contact surfaces of the pivot bearing and sliding bushing are advantageously configured as conically corresponding with one another to ensure a firm seating of the two components on or in one another.

To adjust the degree of friction between the pivot bearing and the sliding bushing, it is proposed according to the invention that the pivot bearing and sliding bushing should be capable of being tensed against one another, with the tensing element configured as a spring element according to a first embodiment of the invention.

According to an alternative embodiment for configuring the tensing element, it is proposed with the invention that the tensing element should be configured as a tensing screw, in particular as a grub or headless screw.

It is further proposed with the invention that oblique contact faces should be configured as centering aids on the rigid partial area and/or on the pivotable partial area of the gripping member. These oblique contact faces allow, first, the components that are to be connected to be pushed onto one another without clamping and, second, also allow a centering of the components in the correct alignment with one another, so that the pivotable partial area of the gripping member can be pushed onto the rigid partial area of the gripping member also when the gripping member is in pivoted position.

It is finally proposed with the invention that the pivot angle of the pivotable partial area should be limited by the mounting of the pivotable partial area, which is eccentric with respect to the longitudinal axis of the gripping member, on the rigid partial area. Limiting the pivot angle of the pivotable partial area of the gripping member is advantageous in preventing any slippage of the gripping member in the operator's hand.

Additional properties and advantages of the invention can be seen from the appended illustrations, in which an embodiment of the inventive medical instrument is presented only by way of example.

BRIEF DESCRIPTION OF THE DRAWINGS

FIG. 1 shows a side view of an inventive medical instrument with the gripping members in a first working position.

FIG. 2 shows a rear view of the depiction in FIG. 1, but showing one gripping member in a pivotable working position.

DETAILED DESCRIPTION OF THE INVENTION

Figure 3:
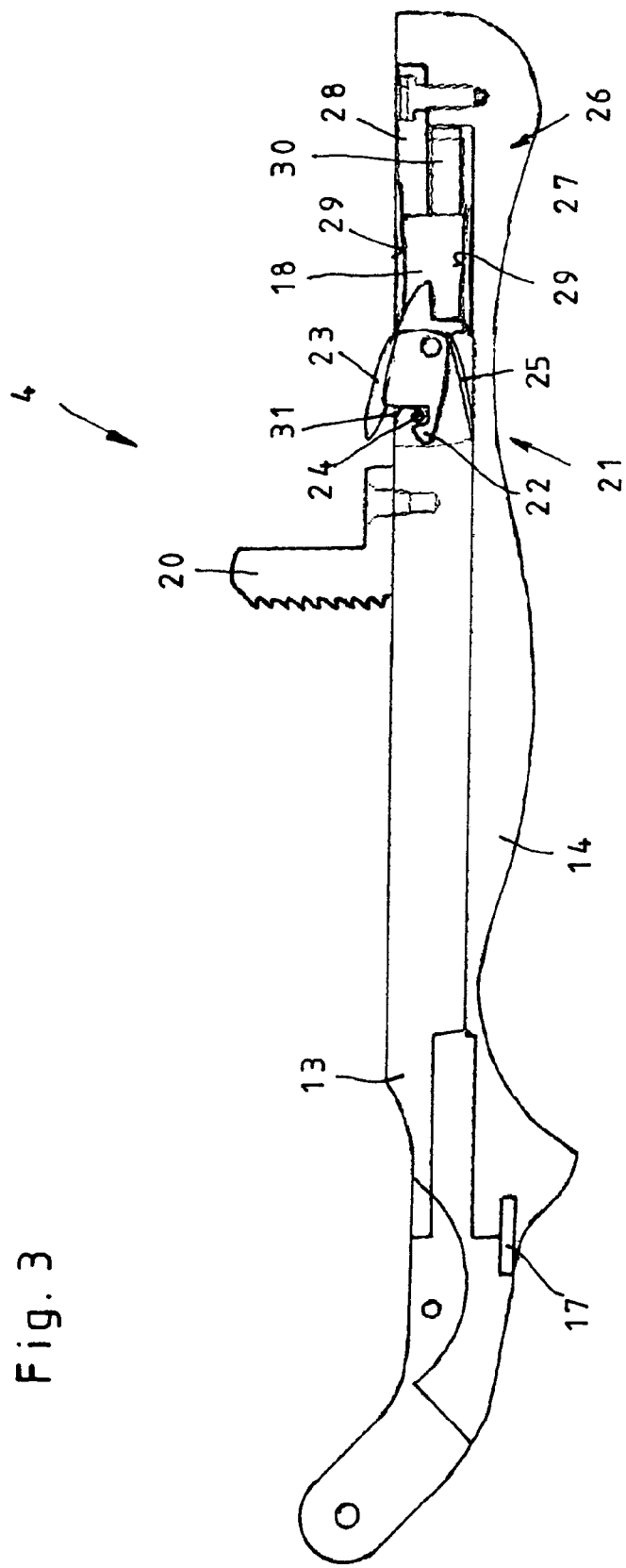
FIG. 3 shows a cut-out side view of the gripping member comprising the pivotable partial area.

The first illustration (FIG. 1) shows the side views of a medical instrument 1 that is configured as a gripping and/or cutting instrument and whose power transmission mechanism has many possible applications, such as for example for punching, cutting, needle holding, gripping instruments, and the like.

The illustrated medical instrument 1 consists essentially of a hollow shaft 2 on whose proximal end a handle 6 is positioned consisting of two gripping members 4 and 5 that can each pivot around related pivot axes 3. Positioned on the distal end of the shaft 2 is a tool 7, which in the illustrated embodiment consists of a jaw member 7a rigidly connected with the shaft 2 and a pivotable jaw member 7b. To open and close the jaw members 7a and 7b of the tool 7 by the actuation of the pivotable gripping members 4 and 5 of the handle 6, the gripping members 4, 5 and the pivotable jaw member 7b are in active connection with one another by means of a push-pull rod 8.

As can further be seen from FIG. 1, the gripping members 4 and 5 are coupled with the push-pull rod 8 in the illustrated embodiment by interposed pivot levers 9, which are mounted so that they can pivot with one free end on a mounting point 10 on each of the gripping members 4, 5 and with the other free end on a common pivot axis 11 on the push-pull rod 8. The articulation of the gripping members 4 and 5 by the pivot levers 9 on the push-pull rod 8 is arranged in such a way that upon pushing together the gripping members 4, 5 the push-pull rod 8 is drawn by the pivot levers 9 to the proximal end of the medical instrument 1, in turn causing a pivoting of the pivotable jaw member 7b of the tool 7 into the closed position.

To open the jaw members 7a, 7b of the tool 7 thus requires the gripping members 4, 5 of the handle 6 to be moved apart, so that the push-pull rod 8 is pressed by the pivot levers 9 to the distal end of the medical instrument 1. To facilitate the pushing apart of the gripping members 4, 5 of the handle 6, a spring element 12 is positioned on the push-pull rod 8 and configured as a push spring by which the gripping members 4, 5 are pre-stressed into the opened position.

To make it possible for the operator, even without releasing or re-gripping the gripping members 4 and 5 of the handle 6, to change the position of the gripping members 4 and 5 in the hand, the gripping member 4 is constructed in two parts, consisting of one rigid partial area 13 and of a partial area 14 that can pivot with respect to the rigid partial area 13, as can be seen in particular from FIG. 2. In the illustrated embodiment the moveable partial area 14 is mounted on the rigid partial area 13 of the gripping member 4 so that it can pivot around a pivot axis 16 positioned eccentrically to the longitudinal axis 15 of the gripping member 4, so that the pivotable mounting of the pivotable partial area 14 occurs by means of a distal mounting pin 17 that is shaped to the rigid partial area 13 and by a proximal pivot bearing 18.

Owing to the eccentric positioning of the pivot axis 16 in relation to the longitudinal axis 15 of the gripping member 4, there automatically occurs a limiting of the pivot angle alpha, around which the pivotable partial area 14 can pivot around the rigid partial area 13 of the gripping member 4, because this eccentricity from a structurally adjustable pivot angle alpha has as a result a clamping motion of the pivotable partial area 14 on the rigid gripping member 13.

FIG. 1 also shows that on the pivotable partial area 14 of the gripping member 4, gripping recesses 19 are hollowed out for inserting the finger or the holding hand, facilitating the gripping and pivoting of the pivotable partial area 14. In addition, a stop mechanism 20 is provided by which the gripping members 4 and 5 of the handle 6 can be affixed to one another when the gripping members 4 and 5 are in the pressed-together position, that is, with the tool 7 in closed position, in order to relieve the operator.

Because impurities can be deposited between the rigid partial area 13 and the pivotable partial area 14 of the gripping member 4, it is necessary to be able to separate the two partial areas 13 and 15 of the gripping member 4 from one another for cleaning purposes. For this purpose, the pivotable partial area 14 of the gripping member 4 can be affixed removably or replaceably to the rigid partial area 13 of the gripping member 4 by means of a catch mechanism 21.

In addition to the possibility of being able to clean the pivotable partial area 14 and the rigid partial area 13 of the gripping member 4 easily and thoroughly, the removable or exchangeable mounting of the pivotable partial area 14 offers the possibility of securing a pivotable partial area 14 that differs in size and/or shape to the partial area 13 of the gripping member 4 if this is required for the purpose and/or desired by the operator.

Figure 4:
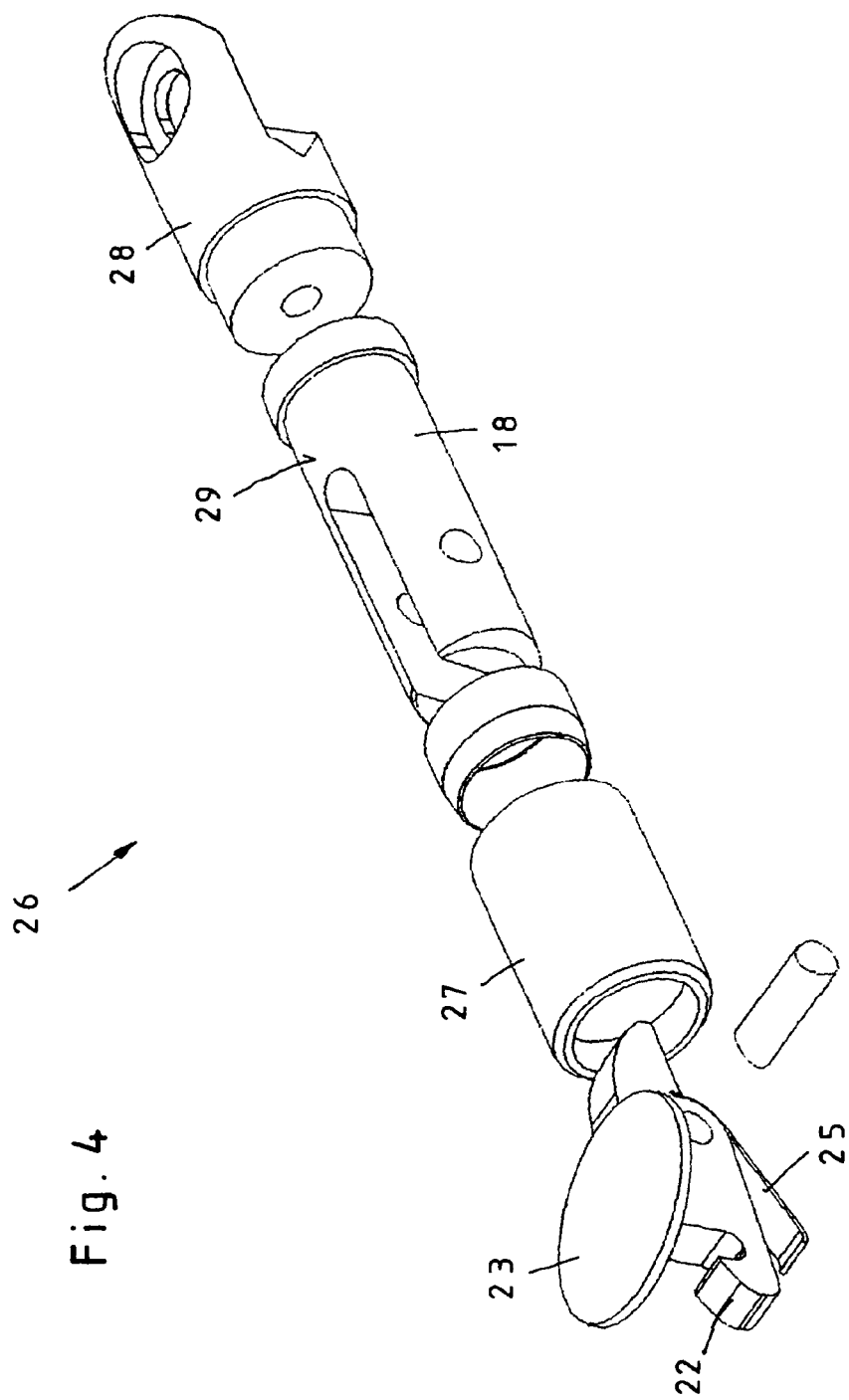
FIG. 4 shows an explosion drawing of the catch mechanism with sliding and locking bushing.

The structure and operation of the catch mechanism 21 can be seen from FIGS. 3 and 4. In the illustrated embodiment, the catch mechanism 21 consists of a spring-loaded push-button 23 that is positioned on the pivotable partial area 14 of the gripping member 4 and equipped with a catch hook 22, and a lock bolt 24 positioned on the rigid partial area 13 of the gripping member 4 and corresponding with the catch hook 22. In the illustrated embodiment of the catch mechanism 21, a leaf spring 25 affixed to the push-button 23 serves as spring element to shift the catch hook 22 into a catch position reaching behind the lock bolt 24.

Alternatively to the illustrated embodiment, it is also possible to position the push-button 23 equipped with the catch hook 22 on the rigid partial area 13 and the lock bolt 24 on the pivotable partial area 14 of the gripping member 4 and/or to configure the component equipped with the catch hook 22 not as a push-button but rather as a slide or lever.

As can be seen further from FIGS. 3 and 4, a sliding and locking bushing 26 is mounted on the push-button 23 and consists of the pivot bearing 18 connected non-pivotably with the push-button 23, of a sliding bushing 27 that is non-pivotably connected with the pivotable partial area 14 and interacting with the pivot bearing 18, and of a tensing member 28 that can be affixed on the pivotable partial area 14. The pivot bearing 18 in this construction forms the proximal mounting of the pivotable partial area 14 of the gripping member 4.

To achieve the least possible friction in the pivot mounting, the contact surfaces 29 of the pivot bearing 18 and of the sliding bushing 27 consist advantageously of a slippery material. Alternatively to the configuration of the contact surfaces from a slippery material, it is also possible to manufacture the pivot bearing 18 and the sliding bushing 27 completely of a slippery material, such as Teflon® for instance.

In the illustrated embodiment the contact surfaces 29 of the pivot bearing 18 and sliding bushing 27 are configured as mutually corresponding cone and countercone in order to ensure a firm seating of the two components on or in one another.

To adjust the degree of friction between the pivot bearing 18 and the sliding bushing 27, the pivot bearing 18 and the sliding bushing 27 can be tensed with respect to one another so that the tensing element 30 in the illustrated embodiment is configured as a grub or headless screw, which can be positioned either centrically or eccentrically to the pivot axis 16 of the pivotable partial area 14.

According to an alternative embodiment, the tensing element 30 can also be configured as a spring element.

On the one hand, to avoid jamming in pushing the pivotable partial area 14 of the gripping member 4, which can be pushed from the proximal end onto the rigid partial area 13 of the gripping member 4, and, on the other hand, to allow also a centering of components 13 and 14 in the correct alignment to one another so that the pivotable partial area 14 of the gripping member 4 can also be pushed onto the rigid partial area 13 of the gripping member 4 when the gripping member 4 is in the pivoted position, oblique contact faces 31 are configured as centering aids on the rigid partial area 13 and/or on the pivotable partial area 14 of the gripping member 4.

Operation of the medical instrument 1, previously described and illustrated in FIGS. 1 to 4, proceeds as follows:

In the starting position shown in FIG. 1, in which the gripping members 4 and 5 of the handle 6 are aligned essentially horizontally and parallel to one another, the operator grips the medical instrument 1, for instance in order to grasp and hold a surgical needle with the tool 7. For this purpose the operator presses together the gripping members 4 and 5 of the handle 6 held with one hand, until the jaw members 7a and 7b are closed.

In order to alter the position of the gripping members 4 and 5 in his or her hand, but without being required to release the handle 6, the operator can pivot the pivotable partial area 14 of the gripping member 4, which is surrounded by the fingers of the holding hand, around the pivot axis 16 as shown in FIG. 2, so that the position of the gripping member 5 on the inner surface of the operator's hand is also altered and thus results in relieving the holding hand.

In the depiction in FIG. 2 the stop mechanism 20 was omitted to make the illustration more transparent.

In addition to relieving the holding hand, the pivotability of at least one partial area 14 of the gripping member 4 has the effect that the operator in each hand position can constantly adjust the gripping members 4 and 5 of the handle 6 in relation to one another, in such a way as to ensure the best possible application of force by the holding hand onto the medical instrument 1.

To dismantle the pivotable partial area 14 of the gripping member 4, for instance for purposes of cleaning or exchanging it with another pivotable partial area 14, the only requirement is to press the push-button 23 downward until the catch hook 22 again releases the lock bolt 24. With the push-button 23 in this pressed-in position, the pivotable partial area 14 of the gripping member 4 can be withdrawn in the proximal direction from the rigid partial area 13 of the gripping member 4.

Assembly of the pivotable partial area 14 on the rigid partial area 13 of the gripping member 4 proceeds in reverse order by pushing the pivotable partial area 14 of the gripping member 4 onto the proximal end of the rigid partial area 13 of the gripping member 4 until the catch hook 22 of the catch mechanism 21 extends around the lock bolt 24 and catches with it.

A medical instrument 1 of this configuration is distinguished in that the pivotable partial area 14 of the gripping member 4 can be removed from the rigid partial area 13 of the gripping member 4 and affixed to it again easily, quickly, and without the assistance of a tool.

What is claimed is:

1. A medical instrument with a shaft on whose distal end a tool is positioned and on whose proximal end a handle is positioned consisting of at least two gripping members, such that the tool can be actuated by a moveably configured gripping member of the handle and such that at least one gripping member of the handle consists of a rigid partial area and a pivotable partial area that can rotate around the rigid partial area, wherein the pivotable partial area of the gripping member is configured to be manually removed from and affixed to the rigid partial area of the gripping member by means of a catch mechanism that serves as a mount for the pivotable partial area, and the catch mechanism comprises a catch hook that is actuated by a push-button and a sliding bushing non-pivotable coupled to the pivotable partial area.

2. A medical instrument according to claim 1, wherein the push-button is spring-loaded.

3. A medical instrument according to claim 1, wherein the push-button is mounted on the catch mechanism.

4. A medical instrument according to claim 3, wherein the catch mechanism includes a pivot bearing connected non-pivotably with the push-button that interacts with the sliding bushing.

5. A medical instrument according to claim 4, wherein at least the contact surfaces of the pivot bearing and of the sliding bushing consist of a slippery material.

6. A medical instrument according to claim 4, wherein the contact surfaces of the pivot bearing and of the sliding bushing are configured so that they correspond conically with one another.

7. A medical instrument according to claim 4, wherein the pivot bearing and the sliding bushing can be tensed with respect to one another by means of a tensing element.

8. A medical instrument according to claim 7, wherein the tensing element is configured as a spring element.

9. A medical instrument according to claim 7, wherein the tensing element is configured as a tensing screw.

10. A medical instrument according to claim 7, wherein the tensing element is configured as a grub or headless screw.

11. A medical instrument according to claim 1, wherein oblique contact faces are configured as centering aids on the rigid partial area and/or on the pivotable partial area of the gripping member.

12. A medical instrument according to claim 1, wherein the pivot angle (alpha) of the pivotable partial area is limited by the mounting of the pivotable partial area on the rigid partial area which is eccentric with respect to the longitudinal axis of the gripping member.

13. A medical instrument according to claim 1, a locking element that is engaged by the catch hook to affix the pivotable partial area to the rigid area.

* * * * *